United States Patent [19]
Roulier et al.

[11] Patent Number: 5,900,241
[45] Date of Patent: May 4, 1999

[54] USE IN COSMETICS OF AN EXPANDED SOLID COMPOSITION WHICH HAS A MATRIX CONTAINING AN ALVEOLAR NETWORK MADE FROM A NATURAL PRODUCT OR FROM A DERIVATIVE OF A NATURAL PRODUCT CAPABLE OF BEING EXPANDED

[75] Inventors: Véronique Roulier, Paris; Myriam Mellul, L'Hays-les-Roses; Gérard Gabin, Paris, all of France; Katrin Holz, Lausanne, Switzerland

[73] Assignee: L'Oreal, Paris, France

[21] Appl. No.: 08/654,866

[22] Filed: May 29, 1996

[30] Foreign Application Priority Data

May 29, 1995 [FR] France ................................... 95 06320
Jun. 16, 1995 [FR] France ................................... 95 07247

[51] Int. Cl.$^6$ ...................................................... A61K 7/00
[52] U.S. Cl. .............................................................. 424/401
[58] Field of Search ............................................. 424/401

[56] References Cited

U.S. PATENT DOCUMENTS 3,800,034  3/1974  Kircher et al. .
4,605,553  8/1986  Passalacqua .
4,748,991  6/1988  Hofman et al. .
4,913,896  4/1990  Harvey .
5,066,486  11/1991  Kamen et al. .
5,679,361  10/1997  Pradier et al. .

FOREIGN PATENT DOCUMENTS

A-0515246  11/1992  European Pat. Off. .
A-0544349  6/1993  European Pat. Off. .
A-0605284  7/1994  European Pat. Off. .
A-1594256  6/1970  France .
WO-A-9208759  5/1992  WIPO .

OTHER PUBLICATIONS

English language Derwent Abstract of EP–A–0605284.
English language Derwent Abstract of EP–A–0515246.

*Primary Examiner*—Robert J. Hill, Jr.
*Attorney, Agent, or Firm*—Finnegan, Henderson, Farabow, Garrett & Dunner, L.L.P.

[57] ABSTRACT

The use in cosmetics of expanded solid compositions whose matrix contains an alveolar network made from a natural product or from a derivative of a natural product capable of being expanded. These compositions constitute novel galenic forms for cosmetic or dermatological use. These compositions may be in the form of rolls, pellets, sheets or flakes which are expanded or in the form of powder. When reduced to a powdered state, these compositions can also be rehydrated or employed as a pulverulent phase in make-up compositions, in particular, in compacted make-up powders.

34 Claims, No Drawings

USE IN COSMETICS OF AN EXPANDED SOLID COMPOSITION WHICH HAS A MATRIX CONTAINING AN ALVEOLAR NETWORK MADE FROM A NATURAL PRODUCT OR FROM A DERIVATIVE OF A NATURAL PRODUCT CAPABLE OF BEING EXPANDED

The present invention relates to the use as cosmetic products of expanded solid compositions whose matrix contains an alveolar network made from a natural product or from a derivative of a natural product capable of being expanded, and to cosmetic and dermatological compositions containing these expanded solid compositions.

Expanded products are known in the food industry which are based on natural substances or on derivatives of natural substances which are capable of being expanded, in particular starch, and on edible ingredients obtained by extrusion in one or a number of single- or twin-screw extruders, in particular aperitif snacks, crisps, cornflakes, cereal-based breakfast products and biscuits.

The Inventors have discovered, surprisingly, novel compositions for cosmetic or dermatological use which are in the form of an expanded solid composition whose matrix contains an alveolar network made from a natural product or from a derivative of a natural product which is capable of being expanded.

The compositions according to the invention may contain inorganic and/or organic fillers. They may themselves constitute novel forms of make-up products such as face powders, mascaras or blushers, novel forms of products for hygiene, such as dry shampoos, or for treatment or care, such as make-up removal products. The compositions of the invention take the appearance of rolls, pellets, sheets or flakes which are expanded and which preferably contain enough fillers to obtain good crumbling and satisfactory softness qualities.

The compositions of the invention may additionally contain large quantities of a fatty phase, making it possible to improve comfort and to facilitate their application to the skin, for example, enabling them to be applied directly without the intermediacy of a make-up tool, e.g., a brush, sponge, or powder puff.

The Inventors have discovered, unexpectedly, that the introduction of large quantities of fillers into an expanded matrix made from a natural product or from a derivative of a natural product capable of being expanded did not significantly decrease the degree of expansion and made it possible to introduce large quantities of fatty substances such as oils and/or waxes into the expanded matrix.

The compositions according to the invention preferably contain, in large quantities, waxes imparting film behavior, slip and matte properties. The compacted powders usually employed for make-up cannot contain large quantities, i.e., more than 10% by weight, of fatty substances such as waxes because their incorporation into powders results in products which cannot be crumbled.

The compositions according to the invention may additionally contain large quantities of fillers which may be difficult to compact, imparting a very soft and nongreasy feel. A filler which is difficult to compact is intended to mean a raw material which, starting at some percentage which will depend on the material in question, cannot be compacted with a mechanical press. Fillers of this type cannot be employed in large concentrations in make-up products in the form of a compacted powder. In addition, make-up products containing them do not exhibit good integrity when stored, good impact strength and/or a suitable planar surface.

As a result of their novel alveolar structure, the compositions of the invention may constitute novel solid galenic forms for make-up in the form of rolls, pellets, sheets or flakes which are expanded and may be applied directly to the skin or the face, or may be reduced to powder and employed conventionally as a make-up powder without exhibiting the above-mentioned disadvantages.

The compositions of the invention may take the form of care and/or hygiene powders which may be applied directly to the skin, the scalp or the hair, for example, as a dry shampoo or free powders for body care.

The compositions of the invention may also take the form of rolls, pellets, sheets or flakes which are expanded, or of a powder, which can be stored in the dry state and is very easily rehydratable after immersion in an aqueous medium in order to reconstitute make-up formulations such as foundations or formulations for care or hygiene, such as creams, milks, bubble baths, gels and shampoos. It is thus possible to incorporate water-sensitive cosmetically active agents into these galenic forms, which are stable in storage at temperatures lower than 45° C.

The compositions according to the invention, stored dry and intended to be rehydrated at the time of use in order to reconstitute cosmetic formulations such as those mentioned above, have the advantage, when compared with the conventional rehydratable galenic forms, of being very easily rehydratable and, in the context of cleansing compositions, especially shampoos, of being less aggressive. since the surfactants are integrated into an expanded matrix.

When reduced to the powder state, the compositions of the invention, can also be employed as a pulverulent phase in the manufacture of make-up products, in particular of compacted powders, and can produce lighter, more homogeneous powders, having a very soft and nongreasy feel, without the above-mentioned disadvantages.

The compositions according to the invention are expanded solid compositions comprising an expanded matrix comprising an alveolar network made from a natural product or from a derivative of a natural product capable of being expanded, and at least one cosmetic or dermatological substance.

The natural products or their derivatives forming the expanded matrix of the compositions according to the invention are preferably chosen from those capable of being expanded by an extrusion process.

Among the natural products and their derivatives capable of being expanded which are preferably employed according to the invention, there may be mentioned vegetable proteins such as soya proteins, gluten proteins, cottonseed proteins; animal proteins such as meat and fish proteins and albumin; proteins derived from dairy products; gelatin; amylose and/or amylopectin and the starch-rich products containing these two constituents, as well as their derivatives.

The starch-rich products are preferred. The starch-rich products are preferably chosen from cereal flours such as wheat, corn, rice, oat, wheatgerm and potato flours; the pure starches commonly employed in foodstuffs such as corn, potato, tapioca and oat starches; starches modified with respect to the amylose/amylopectin ratio such as the product Hylon VII sold by Amylum; starches modified by crosslinking or with a functional group, such as the crosslinked corn starch sold under the name Resistamyl E2 by Amylum, the weakly quaternized corn starch sold under the name Myplus W7 by Amylum; the potato starch sold under the name Supramyl P 60 by Amylum or the hydroxypropylated corn starch sold under the name Merigel EF6 by Amylum.

The compositions according to the invention preferably contain at least one inorganic or organic filler.

The fillers which are preferably employed in the compositions of the invention are cosmetic or dermatological particles which are insoluble in the mixture formed by the starchy matrix.

The fillers are preferably present in the compositions of the invention in concentrations ranging from 2 to 75% by weight relative to the total weight of the composition.

When the fillers have a very low density, in particular lower than 0.1 g cm$^{-3}$, they are preferably present in an amount ranging from 2 to 20% by weight relative to the final composition.

When the fillers have a higher density, in particular greater than 0.5 g cm$^{-3}$, they are preferably present in an amount ranging from 10 to 75% by weight relative to the final composition.

The fillers employed according to the invention are preferably chosen from inorganic or organic fillers, both capable of being of lamellar or spherical structure, or mixtures thereof. The fillers may be easily compactable or difficult to compact.

Each type of filler enables particular and different qualities to be imparted to the composition according to the invention. Thus, for example, fillers of inorganic lamellar type generally impart softness, fillers of inorganic spherical type generally impart good crumbling, and organic spherical fillers generally have a structuring role and impart softness.

Among the fillers of inorganic lamellar type there may preferably be mentioned:

talcs or hydrated magnesium silicates in the form of particles whose dimensions are generally smaller than 40 μm;

micas or aluminosilicates of various compositions, which take the form of flakes which have dimensions ranging from 2 to 200 μm, preferably ranging from 5 to 70 μm, and a thickness ranging from 0.1 to 5 μm, preferably ranging from 0.2 to 3 μm; it being possible for these micas to be of natural origin, for example, muscovite, margarite, roscoelite, lipidolite or biotite, or of synthetic origin. They are generally transparent and make it possible to impart a satin-like appearance to the skin;

clays such as sericites, which belong to the same chemical and crystal class as muscovite, but whose organoleptic properties are close to talc;

kaolin or hydrated aluminum silicate, which takes the form of particles of isotropic forms which have dimensions that are generally smaller than 30 μm and which have good properties of absorption of fatty substances; and boron nitrides.

These inorganic lamellar type fillers are generally compactable.

However, among these fillers of inorganic lamellar type, some are difficult to compact. In this category, it is preferable to mention:

some talcs, such as 'Talc K1' from Nippon or the 'Talc Extra Steamic OOS' from Luzenac;

some sericites, such as the 'Sericite BC282' from Whittaker;

the majority of micatitaniums when they are employed in a high percentage, among which there may preferably be mentioned the mica-nanotitanium 'Cloverleaf PC 2055M' from Ikeda.

Among the compactable fillers of organic lamellar type there may preferably be mentioned the tetrafluoroethylene polymer powders such as 'Fluon' from Montefluos or 'Hostaflonq' from Hoechst.

Among the fillers of organic lamellar type which are difficult to compact there may preferably be mentioned the lauroyllysine 'Aminhope LL-11' from Ajinomoto.

Among the compactable fillers of inorganic spherical type there may preferably be mentioned:

zinc and titanium oxides, generally employed in the form of particles which have dimensions not exceeding a few micrometers (or even smaller than 1 μm in the case of titanium oxide), in particular spherical titanium dioxides such as the 'Spherititan' from Ikeda; these oxides have a smooth feel, good covering power and a high opacity;

precipitated calcium carbonate which, in the form of particles larger than 10 μm in size, has a creamy feel and enables a matte appearance to be obtained;

magnesium carbonate and hydrocarbonate which have, in particular, perfume-fixation properties;

nonporous spherical silica and hydroxyapatite.

Among the fillers of inorganic spherical type which are difficult to compact there may preferably be mentioned:

open-porosity silica microspheres or, more preferably, the hollow silica microspheres such as the 'Silica Beads' from Maprecos, these microspheres being advantageously impregnated with a cosmetic agent; and glass or ceramic 'Macrolite' microcapsules from 3M.

Among the compactable fillers of organic spherical type there may preferably be mentioned:

metal soaps derived from carboxylic organic acids containing from 8 to 22 carbon atoms, preferably from 12 to 18 carbon atoms, for example zinc, magnesium or lithium stearate, zinc laurate or magnesium myristate; these soaps, preferably present in the form of particles which have dimensions smaller than 10 μm, have a smooth feel and make it easier for the powder to adhere to the skin;

powdered unexpanded synthetic polymers such as polyethylene, polyesters, for example, polyethylene isophthalate or terephthalate, and polyamides, for example, nylon, in the form of particles of dimensions smaller than 50 μm, which have absorbent properties and make it possible to give the skin a velvety appearance;

powdered, crosslinked or uncrosslinked, spheronized synthetic polymers like powdered polyacrylic or polymethacrylic acid, powdered polystyrene crosslinked with divinylbenzene and powdered silicone resin, and powdered organic materials of natural origin, like the starch octenylsuccinate sold under the name 'Dry Flow Plus' by Amylum.

Among the fillers of organic spherical type which are difficult to compact there may preferably be mentioned:

microporous polymer microspheres which have a structure similar to that of a sponge; preferably they have a specific surface of at least 0.5 m$^2$/g and, more preferably, of at least 1 m$^2$/g, the specific surface having no upper limit other than that resulting from the practical possibility of producing microspheres of very high porosity; the specific surface may, for example, reach 1000 m$^2$/g or even more. Microspheres of acrylic polymers may also be mentioned, such as those made of 'Polytrap' crosslinked acrylate copolymer from Dow Corning and those of polymethyl methacrylate 'Micropearl M' or 'Micropearl M 100' from Seppic; these microporous microspheres may advantageously be impregnated, in particular with cosmetic active agents; in this connection there may be mentioned the microspheres of styrene-divinylbenzene copolymers, sold under the trade name 'Plastic Powder FPSQ' by Toshiki, which are impregnated with squalane, which is an emollient cosmetic active agent;

polymer microcapsules, which comprise a single closed cavity and form a reservoir which may contain a liquid, especially a cosmetic active agent; they are prepared by known processes such as those described in U.S. Pat. No. 3,615,972 and European Patent Application No. EP-A 0 56219, the disclosures of both of which are incorporated herein by reference. They can be made, for example, of polymers or copolymers of acid, amine or ester monomers containing ethylenic unsaturation, of urea-formaldehyde polymers or of vinylidene chloride polymers or copolymers; by way of example there may be mentioned the microcapsules made of methyl acrylate or methacrylate polymers or copolymers or else of vinylidene chloride and acrylonitrile copolymers; among the latter there will be indicated, in particular, those which contain from 20 to 60% by weight of units derived from vinylidene chloride, from 20 to 60% by weight of units derived from acrylonitrile and from 0 to 40% by weight of other units such as units derived from an acrylic and/or styrene-based monomer. It is also possible to employ acrylic polymers or copolymers which are crosslinked, for example in the case of polymers containing a carboxylic group, with diols used as crosslinking agents; examples which may be mentioned are the vinylidene chloride-acrylonitrile copolymer microcapsules 'Expancel' from Casco Nobel, the 'Q-Max' microcapsules from Q-Max and the '3M' microcapsules from 3M.

The matrix containing the alveolar network formed from a natural product or from a derivative of a natural product capable of being expanded is present in the compositions according to the invention preferably in a proportion ranging from 25 to 98% by weight relative to the weight of the composition.

When the fillers have a very low density, in particular lower than 0.1 g cm$^{-3}$, the starchy expanded matrix preferably represents from 80 to 98% of the total weight of the final composition.

When the fillers have a higher density, in particular greater than 0.5 g cm$^{-3}$, the starchy expanded matrix preferably represents from 25 to 90% of the total weight of the final composition.

The compositions according to the invention may have a water content which is preferably lower than or equal to 5% by weight, and more preferably ranges from 1 to 2% by weight, relative to the weight of the final composition.

The compositions according to the invention additionally preferably contain a fatty phase. This fatty phase preferably includes oils and/or waxes of animal, vegetable, mineral or synthetic origin, by themselves or as mixtures.

Among the oils which are preferably employed, there may be mentioned mink oil, turtle oil, soya oil, grapeseed oil, sesame oil, corn oil, grapeseed oil, sunflower oil, cottonseed oil, avocado oil, olive oil, castor oil, jojoba oil and groundnut oil, hydrocarbon oils such as paraffin oils, squalane and liquid paraffin, fatty esters such as isopropyl myristate, isopropyl palmitate, butyl stearate, hexyl laurate, isononyl isononanoate, 2-ethylhexyl palmitate, 2-hexyldecyl laurate, 2-octyldecyl palmitate, 2-octyldodecyl myristate or lactate, di-2-ethylhexyl succinate, diisostearyl malate and glycerine or diglycerine triisostearate, silicone oils such as polymethylsiloxanes, polymethylphenylsiloxanes, polysiloxanes modified with fatty acids, fatty alcohols or polyoxyalkylenes, fluorinated silicones and perfluorinated oils, higher fatty acids such as myristic acid, palmitic acid, stearic acid, behind acid, oleic acid, linoleic acid, linolenic acid or isostearic acid, and higher fatty alcohols such as cetanol, stearyl alcohol or oleic alcohol.

Among the waxes which are preferably employed in accordance with the present invention, there may be mentioned beeswax, lanolin waxes, China insect waxes, carnauba, candelilla and ouricurry waxes, cork fiber waxes, sugar cane waxes, Japan waxes, hydrogenated jojoba waxes and hydrogenated oils such as hydrogenated sunflower oil, hydrogenated castor oil, hydrogenated copra oil and hydrogenated lanolin, paraffin waxes, microcrystalline waxes, montan waxes and ozokerites, poiyethylene waxes, the waxes obtained by the Fischer-Tropsch synthesis, waxy copolymers and their esters and silicone waxes such as polyalkoxy- and polyalkylsiloxanes.

The fatty phase may be present in proportions which preferably range from 2 to 30% by weight, and more preferably range from 5 to 15% by weight relative to the total weight of the composition.

The fatty phase may additionally preferably include additives such as lipophilic cosmetic active substances and/or liposoluble ingredients which are generally employed in cosmetics, like perfumes. These additives may preferably be present in an amount ranging from 0 to 20% relative to the total weight of the fatty phase.

Besides the fillers, the compositions according to the invention may contain pigments, preferably in a quantity ranging from 0 to 50% by weight relative to the total weight of the final composition. These pigments are preferably chosen from inorganic pigments, organic pigments and pearlescent pigments.

Among the inorganic pigments there may preferably be mentioned, for example, titanium dioxide rutile or anatase), optionally surface-treated, black, yellow, red and brown iron oxides, manganese violet, ultramarine blue, optionally hydrated chromium oxide and ferric blue.

Among the organic pigments there may preferably be mentioned, for example, the pigments D & C Red, D & C Orange, D & C Yellow, carbon black and the lacquers based on cochineal crimson.

The pearlescent pigments may preferably be chosen from white pearlescent pigments such as mica coated with titanium oxide or bismuth oxychloride, colored pearlescent pigments such as micatitanium with iron oxides, micatitanium with ferric blue or chromium oxide, micatitanium with an organic pigment of the above-mentioned type and pigments based on bismuth oxychloride.

The compositions according to the invention may also contain one or a number of nonionic, anionic, cationic or amphoteric surfactants usually employed in cosmetics. The quantity of surface-active agent which may be employed preferably ranges from 2 to 30% relative to the total weight of the composition.

The compositions according to the invention may also preferably contain water-soluble cosmetic active agents.

Among the water-soluble cosmetic active agents which may be preferably used in accordance with the invention, there may be mentioned antioxidant or anti-free radical agents, hydrating or moisturizing agents such as glycerine and collagen and UV-screening agents such as benzophenone. These water-soluble active agents may be present in the final composition in a quantity preferably ranging from 0 to 20%, and more preferably ranging from 5 to 15%, by weight.

The present invention further relates to a process for the preparation of a composition as defined above, which comprises the step of processing the at least one cosmetic or dermatological substance and the natural product or the derivative of a natural product capable of being expanded to form an expanded solid composition comprising a matrix containing an alveolar network.

The present invention still further relates to a process for the preparation of a composition as defined above, characterized in that the composition is obtained from a natural product or from a derivative of a natural product capable of being expanded, from the at least one cosmetic or dermatological substance, and optionally from the other ingredients such as listed above, preferably in the presence of water, by mixing, blending and expansion, preferably by in a twin-screw extruder.

The extruder preferably employed for the process of the invention is preferably chosen from twin-screw extruders such as that described in French Patent Application No. FR 94-00756, the disclosure of which is fully incorporated herein by reference.

The raw materials may be introduced at the entry of the twin-screw extruder, into the feed zone preferably at ambient temperature, more preferably at approximately 20° C., and are then brought into the transport zone at a temperature, preferably of approximately 50° C. and are then blended and compressed in various zones of the extruder which are maintained at a temperature ranging, preferably, from 100 to 160° C.; the mass obtained is conveyed towards the exit of the extruder and is extruded through a die in order to undergo expansion therein to form a matrix.

During the mixing stage, the natural product or the derivative of a natural product capable of being expanded may be gelled and, after extrusion, preferably forms an alveolar network constituting the matrix of the final expanded products.

Another embodiment of the invention comprises novel cosmetic or dermatological compositions comprising an expanded solid composition as defined above.

These compositions may be in the form of rolls, pellets or flakes which are expanded or else may be reduced to powder form. They are capable of easily being rehydrated after immersion in water and capable of reconstituting a liquid or semi-liquid aqueous formulation.

These compositions may be make-up products. They may be applied to the face either directly or by use of a make-up tool such as a brush, a powder puff or an applicator pad. They can be stored in the dry state and, at the time of use, rehydrated after immersion in water to reconstitute a liquid or semi-liquid aqueous make-up formulation, such as a foundation.

The compositions according to the invention may be products for the care and/or hygiene of the skin, the mucous membranes, the scalp or the hair.

They may be in powder form and applied directly to the skin, the scalp or the hair, like, for example, a dry shampoo or a free powder for body care. These compositions may also be in the form of a powder or else of rolls, pellets, sheets or flakes which are expanded, capable of being rehydrated after immersion in water so as to reconstitute an aqueous formulation for care and/or hygiene, such as a cream, a milk, a gel, a bubble bath or a shampoo.

Another subject of the invention refers to the use of an expanded solid composition as defined above in, and for the manufacture of, a cosmetic or dermatological composition.

In particular, the invention relates to the use, as pulverulent phase in, and for the manufacture of, a make-up composition especially in the form of compacted powder such as a blusher or a mascara.

A person skilled in the art will, of course, take care to choose this or these optional additional compound(s) and/or their quantities so that the properties which are advantageously intrinsically attached to the composition in accordance with the invention are not, or are not substantially, damaged by the envisaged addition(s).

The examples which follow are used to illustrate the invention without, however, limiting its scope.

EXAMPLES

Example 1

Dry shampoo in the form of pellets to be rehydrated

The final product had the following formulation:

| | |
|---|---|
| Wheat flour | 35.0% by weight |
| Corn starch | 35.0% by weight |
| Silica sold under the name SB700 by Maprecos | 17.5% by weight |
| Sodium lauryl ether sulphate | 12.5% by weight |

PROCEDURE:

The pellets were obtained by extrusion in a twin-screw extruder. The raw materials were introduced at the entry of the extruder at a temperature of 30° C. They were next brought into the transport zone at a temperature of 50° C. and were then blended and compressed in various zones of the extruder which were maintained at 120° C. The mass thus blended and compressed was conveyed towards the exit of the extruder and was extruded through a die 5 mm in diameter. The speed of rotation of the screws was 500 revolutions/minute. The rolls obtained at the die exit were reduced into the form of pellets having a 3 mm diameter by means of a granulator cutter at the exit of the extruder.

Example 2

Foundations in the form of powder to be rehydrated

The final product had the following formulation:

| | |
|---|---|
| Wheat flour | 40.0% by weight |
| Sesame oil | 5.0% by weight |
| Talc | 25.0% by weight |
| Silica sold under the name SB700 by Maprecos | 25.0% by weight |
| Pigments | 5.0% by weight |

PROCEDURE:

The raw materials were introduced at the entry of a twin-screw extruder at a temperature of 30° C. They were next brought into the transport zone at a temperature of 50° C. and were then blended and compressed in various zones of the extruder which were maintained at 120° C. The mass thus blended and compressed was conveyed towards the exit of the extruder and was extruded through a die 5 mm in diameter. The speed of rotation of the screws was 500 revolutions/minute. The rolls obtained at the die exit were reduced to powder form by means of a conventional rod mill placed at the exit of the extruder.

What is claimed is:

1. A method for cosmetically or hygienically treating the skin, mucous membranes, scalp or hair, which comprises applying to the skin, mucous membranes, scalp or hair, in an amount effective to treat said skin, mucous membranes, scalp or hair, an expanded solid composition having a matrix structure, wherein said matrix comprises an alveolar network formed from a natural product or from a derivative of a natural product, wherein said natural product or said derivative of a natural product is capable of being expanded, and wherein said natural product or said derivative of a natural product capable of being expanded is selected from starch-rich natural products, and their derivatives.

2. A method according to claim 1, wherein said natural product or said derivative of a natural product capable of being expanded is selected from those products capable of being expanded by extrusion.

3. A method according to claim 1, wherein said starch-rich natural products or derivatives thereof are cereal flours, potato flours, pure starches, starches modified with respect to the amyloselamylopectin ratio, crosslinked starches or starches modified with a functional group.

4. A cosmetic or dermatological composition, which comprises at least one cosmetic or dermatological substance and an expanded solid composition having a matrix structure, wherein said matrix comprises an alveolar network formed from a natural product or from a derivative of a natural product, wherein said natural product or said derivative of a natural product is capable of being expanded, and wherein said natural product or said derivative of a natural product capable of being expanded is selected from starch-rich natural products, and their derivatives.

5. A composition according to claim 4, which further comprises an inorganic or organic filler.

6. A composition according to claim 5, wherein said inorganic or organic filler is present in an amount ranging from 2 to 75% by weight relative to the total weight of the composition.

7. A composition according to claim 5, wherein when said inorganic or organic filler has a density lower than 0.1 g cm$^{-3}$, said inorganic or organic filler is present in an amount ranging from 2 to 20% by weight relative to the total weight of the composition and when said inorganic or organic filler has a density higher than 0.5 g cm$^{-3}$, said inorganic or organic filler is present in an amount ranging from 10 to 75% by weight relative to the total weight of the composition.

8. A composition according to claim 5, wherein when said inorganic or organic filler has a density lower than 0.1 g cm$^{-3}$, said matrix comprising an alveolar network represents from 80 to 98% by weight of the total weight of the composition and when said at least one inorganic or organic filler has a density greater than 0.5 g cm$^{-3}$, said matrix comprising an alveolar network represents from 25 to 90% by weight of the total weight of the composition.

9. A composition according to claim 5, wherein said inorganic or organic filler is selected from compactable inorganic or organic fillers of lamellar or spherical structure.

10. A composition according to claim 9, wherein said inorganic or organic filler is a filler of inorganic lamellar structure and is selected from talcs, hydrated magnesium silicates, micas, aluminosilicates, clays, boron nitrides and micatitaniums.

11. A composition according to claim 10, wherein said filler of inorganic lamellar structure is a clay selected from sericites, kaolin and hydrated aluminum silicate.

12. A composition according to claim 9, wherein said inorganic or organic filler is a filler of organic lamellar structure and is selected from tetrafluoroethylene polymer powders and lauroyllysine.

13. A composition according to claim 9, wherein said inorganic or organic filler is a filler of inorganic spherical structure and is selected from zinc oxides, titanium oxides, precipitated calcium carbonate, magnesium carbonate, magnesium hydrocarbonate, nonporous spherical silica, hydroxyapatite, open-porosity and hollow silica microspheres which may be impregnated with a cosmetic active agent, glass microcapsules and ceramic microcapsules.

14. A composition according to claim 9, wherein said inorganic or organic filler is a filler of organic spherical structure and is selected from metal soaps derived from carboxylic organic acids containing from 8 to 22 carbon atoms; zinc laurate; magnesium myristate; powdered unexpanded synthetic polymers; powdered crosslinked and uncrosslinked, spheronized synthetic polymers; powdered organic materials; microporous polymer microspheres which may be impregnated with cosmetic active agents, and polymer microcapsules which may be crosslinked.

15. A composition according to claim 14, wherein said filler of organic spherical structure is a metal soap derived from carboxylic organic acids containing from 8 to 22 carbon atoms and is selected from zinc stearate, magnesium stearate and lithium stearate.

16. A composition according to claim 4 wherein said natural product or said derivative of a natural product capable of being expanded is selected from those products capable of being expanded by extrusion.

17. A composition according to claim 16, wherein said starch-rich natural products or derivatives thereof are cereal flours, potato flours, pure starches, starches modified with respect to the amylose/amylopectin ratio, crosslinked starches or starches modified with a functional group.

18. A composition according to claim 4, wherein said matrix represents from 25 to 98% by weight of the total weight of the composition.

19. A composition according to claim 4, which further comprises water in an amount lower than 5% by weight relative to the total weight of the composition.

20. A composition according to claim 19, wherein said water content ranges from 1 to 2% by weight relative to the total weight of the composition.

21. A composition according to claim 4, which further comprises a fatty phase.

22. A composition according to claim 21, wherein said fatty phase represents from 2 to 30% by weight relative to the total weight of the composition.

23. A composition according to claim 22, wherein said fatty phase represents from 5 to 15% by weight relative to the total weight of the composition.

24. A composition according to claim 21, wherein said fatty phase comprises at least one oil or wax of animal, vegetable, mineral or synthetic origin.

25. A composition according to claim 4, wherein said cosmetic or dermatological substance is selected from pigments, surfactants, liposoluble active agents, liposoluble cosmetic additives, antioxidants, agents against free radicals, hydrating agents, moisturizers and sunscreens.

26. A composition according to claim 4, which is in the form of a roll, a pellet, a sheet or a flake wherein said roll, pellet, sheet or flake is expanded to a matrix or reduced to powder form.

27. A composition according to claim 26, which is capable of being rehydrated after immersion in water and capable of reconstituting a liquid or semi-liquid aqueous formulation.

28. A composition according to claim 26, which is a make-up product.

29. A composition according to claim 26, which is a product for the care and/or hygiene of the skin, the mucous membranes, the scalp or the hair.

30. A process for the preparation of a composition according to claim 4, which comprises the steps of:

mixing said at least one cosmetic or dermatological substance and said natural product or said derivative of a natural product capable of being expanded, blending said mixture, compressing said blended mixture and extruding said compressed mixture through a die in a twin-screw extruder to form a matrix containing an alveolar network.

31. A process according to claim 30, wherein prior to said mixing step, said at least one cosmetic or dermatological substance and said natural product or said derivative of a natural product capable of being expanded are introduced at the entry of said extruder at ambient temperature and are then brought into the transport zone of said extruder at a temperature of approximately 50° C., said ingredients are then mixed, blended, and compressed in various zones of said extruder which are maintained at a temperature ranging from 100 to 160° C., said compressed mixture is then conveyed towards the exit of said extruder and is extruded through a die in order to undergo expansion to form a matrix.

32. A method for the preparation of a cosmetic or a dermatological formulation, which comprises including in said formulation a cosmetic or dermatological composition according to claim 4.

33. A method for the preparation of a make-up formulation which comprises reducing a cosmetic or dermatological composition according to claim 4 to powder form and including said powder in said make-up formulation as a pulverulent phase.

34. A process for the preparation of a composition according to claim 4, which comprises the step of:

processing said at least one cosmetic or dermatological substance and said natural product or said derivative of a natural product capable of being expanded to form an expanded solid composition comprising a matrix containing an alveolar network.

* * * * *

UNITED STATES PATENT AND TRADEMARK OFFICE
CERTIFICATE OF CORRECTION

PATENT NO. : 5,900,241

DATED : May 4, 1999

INVENTOR(S) : ROULIER et al.

It is certified that error appears in the above-indentified patent and that said Letters Patent is hereby corrected as shown below:

In claim 3, column 9, line 18, "amyloselamylopectin" should read --amylose/amylopectin--.

Signed and Sealed this

Twenty-third Day of November, 1999

Attest:

Q. TODD DICKINSON

*Attesting Officer*   *Acting Commissioner of Patents and Trademarks*